United States Patent [19]

Buchi

[11] 4,032,577

[45] June 28, 1977

[54] UNSATURATED KETONES

[75] Inventor: George Buchi, Cambridge, Mass.

[73] Assignee: Hoffmann-La Roche Inc., Nutley, N.J.

[22] Filed: Apr. 28, 1976

[21] Appl. No.: 680,949

Related U.S. Application Data

[62] Division of Ser. No. 547,688, Feb. 6, 1975, Pat. No. 3,935,440, which is a division of Ser. No. 158,080, June 29, 1971, Pat. No. 3,884,970.

[52] U.S. Cl. ............................................. 260/594
[51] Int. Cl.² ...................................... C07C 49/24
[58] Field of Search .................................... 260/594

[56] References Cited

UNITED STATES PATENTS

| | | | |
|---|---|---|---|
| 2,091,373 | 8/1937 | Nellis | 260/594 |
| 2,124,686 | 7/1938 | Carothers et al. | 260/594 |
| 2,957,889 | 10/1960 | Hoaglin et al. | 260/594 |

OTHER PUBLICATIONS

Weygand et al., "Preparative Organic Chemistry" pp. 400–403 (1973).

*Primary Examiner*—Bernard Helfin
*Assistant Examiner*—James H. Reamer
*Attorney, Agent, or Firm*—Samuel L. Welt; Bernard S. Leon; William H. Epstein

[57] ABSTRACT

This invention relates to a process for the preparation of 2-alkenyl-4-hydroxy-3-methyl-2-cyclopenten-1-ones from the reaction product of 2,4-pentane dione and a 2-propen-or 2-propyn-1-ol derivative including intermediates therein.

3 Claims, No Drawings

UNSATURATED KETONES

This is a division of application Ser. No. 547,688 filed Feb. 6, 1975, now U.S. Pat. No. 3,935,440, which in turn is a divisional application of Ser. No. 158,080 filed June 29, 1971, now U.S. Pat. No. 3,884,970.

BACKGROUND OF THE INVENTION

The class of compounds commonly referred to as pyrethrins is generally understood to include the four major active ingredients of pyrethrum viz. Pyrethrin I, Cinerin I, Pyrethrin II and Cinerin II. Pyrethrum is the commercial extract of the herbaceous perrennial *Chrysanthemum cinerariaefolium* and is an important source of natural insecticides. The pyrethrins which, as noted above, comprise the major insecticidal constituents of pyrethrum and are especially useful insecticides by virtue of their increased insecticidal potency when used with known synergists, e.g., piperonyl butoxide, their low mammalian toxicity, rapid knockdown or paralytic properties, and the absence of induced insect resistance from exposure to sublethal doses.

Owing to their importance, the preparation of pyrethrins has been the subject of much investigation. There are, however, no commercially acceptable syntheses available for the preparation of the pyrethrins and the entire commercial production of pyrethrins is accomplished by extraction from pyrethrum flowers. Such commercial extraction procedures involve treatment with organic solvents which invariably results in the extraction of substantial amounts of inactive and undesirable impurities necessitating costly and cumbersome purifications in order to obtain insecticidally useful pyrethrins. The novel process of this invention provides a method for the synthesis of several of the pyrethrins and pyrethrin analogs via easily accessible starting materials.

DETAILED DESCRIPTION OF THE INVENTION

This invention pertains to a novel chemical synthesis of a 2-alkenyl-4-hydroxy-3-methyl-2-cyclopenthen-1-one of the formula:

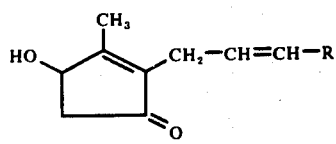     I wherein R is hydrogen, lower alkyl or lower alkenyl.

The compound of formula I can be prepared from the reaction of 2,4-pentadione and a 2-propen- or 2-propyn-1-ol derivative of the formula:

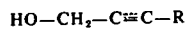     II wherein R is as above and the dotted bond can be optionally hydrogenated by the following reaction scheme:

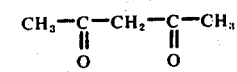     III

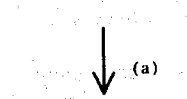

↓ (a)

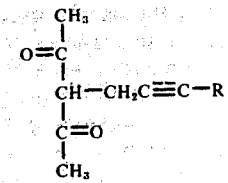     IV

↓ (b)

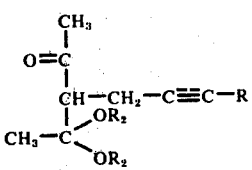     V

↓ (c)

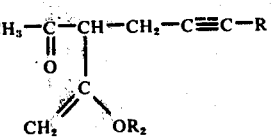     VI

↓ (d)

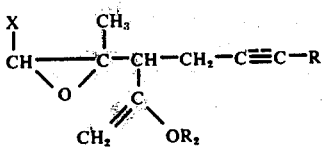     VII

↓ (e)

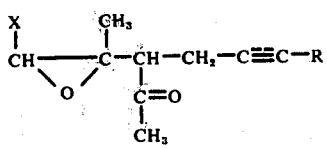     VIII

↓ (f)

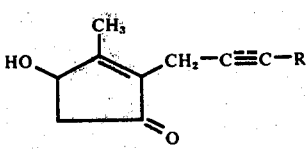     I-A wherein R is as above; X is a halogen; $R_2$ is lower alkyl and the dotted bond can be optionally hydrogenated.

In reacting the compound of formula II with the compound of formula III to produce a compound of the formula IV via reaction step (a), the hydroxy group on the compound of formula II is converted to a leaving group. This is accomplished by reacting the hydroxy group on the compound of formula II with an acid halide to form a leaving group. the acid halides suitable for forming leaving groups are the halides of organic sulfonic acids such as p-toluene sulfonic acid and lower alkyl sulfonic acid.

Especially preferred as the leaving group in the 11-position is the p-toluene sulfonyloxy group such as tosyloxy, lower alkyl sulfonyloxy, such as mesyloxy.

The compound of formula II containing a leaving group is reacted with the compound of formula III in the presence of a base. Any conventional base can be utilized in carrying out this reaction. Among the preferred bases which can be utilized are the tertiary amine bases such as the tri(lower alkyl) amines, heterocyclic amine bases such as pyridine, etc. Among the tertiary amine bases, compounds such as N,N-diisopropyl ethyl amine, triethyl amine, trimethylamine, etc. are generally preferred. In carrying out this reaction, temperature and pressure are not critical and this reaction can be carried out at room temperature and atmospheric pressure. Generally, it is preferred to utilize temperatures of from about −30° C. to 30° C. Generally, this reaction is carried out in the presence of an aqueous reaction medium containing a water miscible organic solvent. Any conventional water miscible organic solvent such as the lower alkanols can be utilized. Among the organic solvents, methanol is preferred.

In the reaction of step (a), the compound of formula IV can be isolated from the reaction medium by means of a chelating agent. Any conventional chelating agent such as cupric acetate monohydrate can be utilized to isolate the compound of formula IV in pure form from its reaction medium. The chelate can be converted to the compound of formula IV by treatment with a mineral acid such as sulfuric acid. Any conventional means for regenerating the components of a chelate can be utilized in carrying out this reaction.

The compound of formula IV is converted to the compound of formula V, via reaction step (b) by treating the compound of formula IV with a compound of the formula:

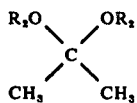

wherein $R_2$ is as above.

Generally, this reaction is carried out by heating the reaction to temperature below 65° C. Any inert organic solvent can be utilized in the reaction medium. Solvents such as lower alkanols, aromatic hydrocarbons such as benzene, etc. can be utilized. When a lower alkanol is utilized as the solvent, this lower alkanol should be an alcohol having the formula: $R_2OH$ wherein $R_2$ is the same alkyl group as in the compound of formula X. Generally, this reaction is carried out in the presence of an acid catalyst. Any conventional acid catalyst can be utilized. Generally, it is preferred to utilize p-toluene sulfonic acid as the acid catalyst. The reaction of step (b) is carried out by distilling the reaction medium at a temperature of below 65° C. Generally, it is preferred to distill the reaction mixture at temperatures of from 40° to 65° C.

The compound of formula VI is converted to the compound of formula VII via reaction step (d) by treating the compound of formula VI with a lower alkyl lithium and a methylene halide. Among the preferred alkyl lithiums for carrying out this reaction is n-butyl lithium. Among the preferred methylene halides for carrying out this reaction is methylene chloride. Generally, this reaction is carried out at a temperature of from −70° C. to −100° C. This low temperature can be maintained by utilizing a liquid nitrogen atmosphere. In carrying out this reaction, any conventional inert organic solvent having a freezing point of lower than −70° C. can be utilized. Among the preferred solvents are the ether solvents such as tetrahydrofuran and diethyl ether.

The compound of formula VII can be converted to the compound of formula VIII via reaction step (e). This reaction can be carried out by treating the compound of formula VII with a mineral acid, preferably a dilute mineral acid such as 10% by weight aqueous hydrochloric acid. Any conventional mineral acid can be utilized in carrying out this reaction. Generally, this reaction is carried out in a solvent medium containing water. This solvent medium can contain an inert water miscible organic solvent. Any conventional inert water miscible organic solvent can be utilized in carrying out this reaction. Among the preferred solvents are the ether solvents such as dioxane, tetrahydrofuran, etc. In carrying out this reaction temperature and pressure are not critical and room temperature and atmospheric pressure can be utilized.

The compound of formula VIII can be converted to the compound of formula I-A via reaction step (f) by treating the compound of formula VIII with a base. Any conventional base can be utilized in carrying out this invention. Among the conventional bases are included the alkali metal hydroxides such as sodium hydroxide, potassium hydroxide, etc.; the alkaline earth metal hydroxides such as calcium hydroxide, barium hydroxide, etc. Generally, this reaction is carried out in an aqueous medium. If desired, a water miscible organic solvent can be present in the reaction medium. Among the water miscible organic solvents which can be present, the lower alkanols such as methanol are preferred. In carrying out this reaction, temperature and pressure and not critical and this reaction can be carried out at room temperature and atmospheric pressure. On the other hand, elevated or reduced temperatures can be utilized. Generally, it is preferred to carry out this reaction at a temperature of from 0° C. to 70° C.

In accordance with this invention, the compounds of formula II, IV, V, VI, VII, VIII and I-A, where the dotted bond is not hydrogenated, can be reduced by partial hydrogenation to the olefinic double bond at any stage of the process. Any conventional method of partial hydrogenation can be utilized in carrying out this reaction. For example, these compounds can be catalytically hydrogenated in an inert solvent such as ethyl acetate, toluene or petroleum ether in the presence of a selective hydrogenation catalyst, e.g., a palladium-lead catalyst in the presence of quinoline of the type disclosed in QLV) Chim. Acta, 35, 446 (1952).

In accordance with this invention, it is generally preferred to partially hydrogenate the acetylenic compounds of formula V, VI, VII, VIII and I-A. It has been found that the use of a selective hydrogenation catalyst such as palladium deactivated with lead produces a cis configuration across the resulting double bond. Therefore, by use of 2-propyn-1-ol of the formula II, the above process provides a means for stereo-specifically producing pyrethrins.

Utilizing the process of this invention, one can convert 2-butyn-1-ol to 2-(but-2-enyl)-3-methyl-4- hydroxy-2-cyclopenten-1-one (Cinerolone); 2-propyn-1-ol to 2-allyl-3-methyl-4-hydroxy-2-cyclcopenten-1-one (allethrolone); 3-pentyn-1-ol to 1-(pent-2-enyl)-3-methyl-4-hydroxy-2-cyclopent-1-one (jasmolone); and 1,3-pentadien-5-ol to 2-(2,4-pentadienyl)-3-methyl-4-hydroxy-2-cyclopenten-1-one.

Conversion of the 2-alkenyl-3-methyl-4-hydroxy-2-cyclopenten-1-one, products of formula I to the insecticidally useful pyrethrins and pyrethrin analogs is readily accomplished by esterification with appropriate cyclopropane carboxylic acid, e.g., chrysanthemum monocarboxylic acid (chrysanthemic acid), pyrethic acid and the like, which are known in the art. The preparation of pyrethrins and pyrethrin analogs by esterification of substituted 3-methtyl-4-hydroxy-2-cyclopenten-1-ones with cyclopropane carboxylic acid has been described, for example, by, among others, L. Crombie et al., J.C.S. p. 3963 (1956); L. Crombie et al., J.C.S. p. 1152 (1950) and Schecter et al., J.A.C.S. 71, 3165 (1949).

As used throughout the instant specification, the term halogen designates all four halogens, i.e., chlorine, bromine, iodine, and fluorine, with chlorine being preferred. The term "lower alkyl" designates lower alkyl groups containing from 1 to 7 carbons such as methyl, ethyl, propyl, 1-propyl, etc. The term "lower alkenyl" comprehends lower alkenyl groups containing from 2 to 7 carbon atoms such as vinyl, allyl, etc.

The invention will be more fully understood from the specific examples which follow. These examples are intended to be illustrative of the invention, and are not to be construed as limitative thereof. The temperatures in these examples are in degrees centigrade and the ether utilized is diethyl ether.

EXAMPLE 1

Preparation of 3-acetyl-5-heptyn-2-one

A solution of 75.0 g. (0.75 mol.) of 2,4-pentanedione, 113 g. (0.50 mol.) 2-butyl-p-toluenesulfonate and 97.0 g. (0.75 mol.) of N,N-diisopropyl ethyl amine in 100 ml. of water and 150 ml. of methanol was briefly stirred at 0° and then at room temperature for 24 hours, cooled in an ice bath, made just acidic with dilute hydrochloric acid, diluted with water (300 ml.) and extracted with diethyl ether (4 × 200 ml.). The combined ethereal extracts were washed with 200 ml. each of water and saturated aqueous sodium chloride, dried (MgSO$_4$), concentrated, and distilled under reduced pressure to remove excess 2,4-pentanedione. To the residue dissolved in 100 ml. of methanol was added a hot filtered solution of 50 g. (0.25 mol.) of cupric acetate monohydrate in 375 ml. of water. After being cooled overnight in a refrigerator, the suspension was filtered and washed with methanol and diethyl ether to give 3-acetyl-5-heptyn-2-one as a gray copper salt. The salt was stirred vigorously with 500 ml. of 20% aqueous sulfuric acid and 400 ml. of diethyl ether until consumed, the ether layer removed and the blue aqueous phase extracted with ether (3 × 200 ml.). The combined ethereal layer and extracts were washed with 200 ml. each of water and saturated aqueous sodium chloride, dried (MgSO$_4$), and concentrated to afford 3-acetyl-5-heptyn-2-one as a yellow oil. Distillation gave a pale yellow oil; B.P. 85° . (2.6 mmHg).

EXAMPLE 2

Preparation of 2-methoxy-3-acetyl-1-hepten-5-yne

A solution of 38.0 g. (0.25 mol.) of 3-acetyl-5-heptyn-2-one, 32.3 g. (0.31 mol.) of 2,2-dimethoxy-propane, and 5 mg. of p-toluenesulfonic acid in 25 ml. of absolute methanol and 25 ml. of benzene was slowly distilled until the material boiling below 65° had been removed, then stirred with 1 g. of sodium carbonate and filtered to produce 2,2-dimethoxy-3-acetyl-5-heptyne in the filtrate.

Distillation of the filtrate afforded 25.9 g. of a pale yellow oil, b.p. 77°–82° (2.0 mmHg). The distillate was dissolved in 100 ml. of ether, washed with ice-cold 2% by weight aqueous sodium hydroxide (3 × 35 ml.), water, and saturated aqueous sodium chloride, dried (Na$_2$SO$_4$), concentrated and distilled to yield 2-methoxy-3-acetyl-1-hepten-5-yne; b.p. 81°–83° (2.0 mmHg).

EXAMPLE 3

Preparation of (Z)-2-methoxy-3-acetyl-1,5-heptadiene

A mixture of 9.96 g. (60 mmol.) of 2-methoxy-3-acetyl-1-hepten-5-yne, 0.50 g. of Lindlar catalyst, and 10 drops of synthetic quinoline in 100 ml. of ethyl acetate was stirred under one atmosphere of hydrogen until hydrogen absorption was complete, then filtered, concentrated and distilled to afford (Z)-2-methoxy-3-acetyl-1,5-heptadiene; b.p. 64°–66°, (2.0 mmHg).

EXAMPLE 4

Preparation of (Z)-1-chloro-1,2-epoxy-2-methyl-3-(1-methoxyethenyl)-5-heptene A solution of 28 ml. (45 mmol.) of 1.6 M n-butyl lithium in hexane was added dropwise and with stirring during 45 minutes to a solution of 3.2 ml. (50 mmol.) of methylene chloride in 20 ml. of diethyl ether, 20 ml. of petroleum ether, and 140 ml. tetrahydrofuran under nitrogen cooled to −95° in a toluene-liquid nitrogen slush. After 30 minutes, a solution of 6.72 g. (40 mmol.) of (Z)-2-methoxy-3-acetyl-1,5-heptadiene in 60 ml. of tetrahydrofuran was added dropwise during 45 minutes and the mixture was allowed to warm slowly to room temperature and then allowed to reflux for 3 hours. The mixture was then cooled, concentrated, poured into 200 ml. of saturated aqueous ammonium chloride, extracted with diethyl ether, the combined ethereal extracts washed with saturated aqueous sodium chloride, dried (Na$_2$SO$_4$) and concentrated to afford (Z)-1-chloro-1,2-epoxy-2-methyl-3-(1-methoxyethenyl)-5-heptene.

EXAMPLE 5

Preparation of (Z)-1-chloro-1,2-epoxy-2-methyl-3-acetyl-5-heptene

A solution of 6.75 g. (31.5 mmol.) of crude (Z)-1-chloro-1,2-epoxy-2-methyl-3-(1-methoxy-ethenyl)-5-heptene in 350 ml. of 2:1 tetrahydrofuran: 10% by weight aqueous hydrochloric acid was stirred at room temperature for 30 minutes, concentrated, extracted with diethyl ether, the ethereal extracts washed with water and saturated aqueous sodium chloride, dried (Na$_2$SO$_4$) and concentrated to afford (Z)-1-chloro-1,2-epoxy-2-methyl-3-acetyl-5-heptene as a yellow oil.

EXAMPLE 6

Preparation of (±)cis-Cinerolone

A solution of 4.15 g. (20 mol) of crude (Z)-chloro-1,2-epoxy-2-methyl-3-acetyl-5-heptene and 6.30 g. (20 mol.) of barium hydroxide octahydrate in 200 ml. of 50% aqueous methanol was stirred at room temperature under argon for 1 hour, neutralized with dilute hydrochloric acid, concentrated, extracted with ether, the extract washed with water and saturated aqueous sodium chloride, dried ($Na_2SO_4$), concentrated and distilled to afford (±)cis-Cinerolone as an oil, b.p. 95°–100° (0.05 mmHg)

I claim:

1. A compound of the formula:

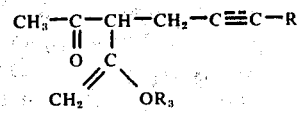

wherein R is hydrogen, lower alkenyl or lower alkyl; $R_3$ is lower alkyl, and the dotted bond can be optionally hydrogenated.

2. The compound of claim 1 wherein said compound is 2-methoxy-3-acetyl-1-hepten-5-yne.

3. The compound of claim 1 wherein said compound is 2-methoxy-3-acetyl-1,5-heptadiene.

* * * * *